United States Patent
Snell et al.

(10) Patent No.: US 8,882,837 B2
(45) Date of Patent: Nov. 11, 2014

(54) HIGH PRECISION MANUFACTURE OF POLYURETHANE PRODUCTS SUCH AS SPINAL DISC IMPLANTS HAVING GRADUAL MODULUS VARIATION

(75) Inventors: Robert Snell, Suffolk (GB); Geoffrey Thomas Andrews, Cambridge (GB); Martin Cable, Cambridgeshire (GB); Scott Johnson, Cambridgeshire (GB)

(73) Assignee: Ranier Limited, Cambridge (GB)

( * ) Notice: Subject to any disclaimer, the term of this patent is extended or adjusted under 35 U.S.C. 154(b) by 772 days.

(21) Appl. No.: 11/505,633

(22) Filed: Aug. 17, 2006

(65) Prior Publication Data

US 2007/0050038 A1 Mar. 1, 2007

Related U.S. Application Data

(63) Continuation of application No. 10/530,919, filed as application No. PCT/GB03/04352 on Oct. 8, 2003, now Pat. No. 8,353,960.

(30) Foreign Application Priority Data

Oct. 8, 2002 (GB) .................................. 0223327.8

(51) Int. Cl.
*A61F 2/44* (2006.01)
(52) U.S. Cl.
USPC ....................................................... 623/17.12
(58) Field of Classification Search
USPC .......................... 623/1.11–1.54, 17.11–17.16
See application file for complete search history.

(56) References Cited

U.S. PATENT DOCUMENTS

| | | | |
|---|---|---|---|
| 3,867,728 A | 2/1975 | Stubstad et al. | |
| 3,905,582 A | 9/1975 | Fiorentini | |
| 4,834,757 A | 5/1989 | Brantigan | |
| 4,911,718 A * | 3/1990 | Lee et al. | 623/17.15 |
| 5,071,437 A | 12/1991 | Steffee | |
| 5,171,281 A | 12/1992 | Parsons et al. | |
| 5,306,309 A | 4/1994 | Wagner et al. | |
| 5,514,180 A | 5/1996 | Heggeness et al. | |
| 5,534,030 A | 7/1996 | Navarro et al. | |
| 5,545,229 A * | 8/1996 | Parsons et al. | 623/17.15 |
| 5,609,803 A | 3/1997 | Addeo et al. | |
| 5,645,596 A | 7/1997 | Kim et al. | |
| 5,676,670 A * | 10/1997 | Kim | 606/108 |

(Continued)

FOREIGN PATENT DOCUMENTS

| | | |
|---|---|---|
| EP | 0464514 B1 | 1/1992 |
| EP | 0464886 A2 | 1/1992 |

(Continued)

OTHER PUBLICATIONS

International Search Report from PCT/GB03/04352, mailed May 2, 2004.

(Continued)

*Primary Examiner* — David Isabella
*Assistant Examiner* — Ann Schillinger
(74) *Attorney, Agent, or Firm* — Wolf, Greenfield & Sacks, P.C.

(57) ABSTRACT

A process for making a polymeric product having a gradual variation in modulus through at least a portion of the product is disclosed together with an artificial spinal disc formed using the process.

26 Claims, 7 Drawing Sheets

(56) References Cited

U.S. PATENT DOCUMENTS

| | | |
|---|---|---|
| 5,824,094 A | 10/1998 | Serhan et al. |
| 6,139,579 A | 10/2000 | Steffee et al. |
| 6,162,252 A | 12/2000 | Kuras et al. |
| 6,248,131 B1 | 6/2001 | Felt et al. |
| 6,302,916 B1 | 10/2001 | Townley et al. |
| 6,348,071 B1 | 2/2002 | Steffee et al. |
| 6,482,234 B1 | 11/2002 | Weber et al. |
| 6,592,624 B1 | 7/2003 | Fraser et al. |
| 6,641,614 B1 * | 11/2003 | Wagner et al. ............. 623/17.15 |
| 6,679,915 B1 | 1/2004 | Cauthen |
| 6,723,097 B2 | 4/2004 | Fraser et al. |
| 6,987,136 B2 | 1/2006 | Erbe et al. |
| 7,008,452 B2 | 3/2006 | Hawkins |
| 7,060,100 B2 | 6/2006 | Ferree et al. |
| 7,201,776 B2 | 4/2007 | Ferree et al. |
| 2002/0082701 A1 | 6/2002 | Zdeblick et al. |
| 2003/0023311 A1 | 1/2003 | Trieu |
| 2003/0040800 A1 * | 2/2003 | Li et al. ..................... 623/17.12 |
| 2003/0100951 A1 | 5/2003 | Serhan et al. |
| 2003/0204261 A1 * | 10/2003 | Eisermann et al. ........ 623/17.14 |
| 2004/0049002 A1 | 3/2004 | Andrews et al. |
| 2004/0049170 A1 | 3/2004 | Snell |
| 2004/0054413 A1 | 3/2004 | Higham et al. |
| 2004/0133278 A1 | 7/2004 | Marino et al. |
| 2005/0015150 A1 | 1/2005 | Lee |
| 2005/0165485 A1 | 7/2005 | Trieu |
| 2006/0111785 A1 | 5/2006 | O'Neil |
| 2006/0167550 A1 | 7/2006 | Snell et al. |
| 2006/0241759 A1 | 10/2006 | Trieu |
| 2007/0032874 A1 | 2/2007 | Lee et al. |
| 2007/0043443 A1 | 2/2007 | Snell et al. |
| 2007/0050032 A1 | 3/2007 | Gittings et al. |
| 2007/0050037 A1 | 3/2007 | Snell et al. |
| 2007/0276492 A1 | 11/2007 | Andrews et al. |

FOREIGN PATENT DOCUMENTS

| | | |
|---|---|---|
| EP | 0627204 A2 | 12/1994 |
| WO | WO 93/16664 | 9/1993 |
| WO | WO 02/11975 A1 | 2/2002 |

OTHER PUBLICATIONS

Bao, Q., et al., "The artificial disc: theory, design and materials" *Biomaterials* (1996) 1157-1167, vol. 17, No. 12, Elsevier Science Limited, Great Britain.

Unterberger, M., et al., "Produktionsparameter beim RRIM-Prozeß kontinuierlich überwachen", *Kunststoffe*, 80 Aug. 1990, No. 8, Munchen, DE.

* cited by examiner

HIGH PRECISION MANUFACTURE OF POLYURETHANE PRODUCTS SUCH AS SPINAL DISC IMPLANTS HAVING GRADUAL MODULUS VARIATION

CROSS-REFERENCE TO RELATED APPLICATIONS

This application is a continuation of U.S. application Ser. No. 10/530,919, filed on Apr. 8, 2005, which claims the benefit of and priority to PCT Application No. PCT/GB2003/004352, filed on Oct. 8, 2002, the entire contents of each of which are incorporated herein by reference.

The present invention relates to a method of manufacturing a polymeric product and to a product for medical use made in accordance with the method. An example of a component made from the material and using the method of the invention is an artificial spinal disc or disc spacer used to replace a displaced or damaged intervertebral disc in the spine of a patient although the invention is also applicable to the manufacture of replacement joints in addition to other surgical instrumentation and components for the healthcare industry.

Although reference will now be made primarily to the application of the invention in the manufacture of an artificial spinal disc, the invention is not limited to an artificial spinal disc or the specific method of making such a disc, as has already been mentioned above.

Approximately one third to a quarter of the length of an adult human spine is occupied by the vertebral discs. Each disc comprises an annular wall (annulus fibrosus) that surrounds and contains a central nucleus (nucleus pulposus) filled with gelatinous material that occupies approximately 30 to 50% of the cross sectional area of the disc. The annular wall is a concentrically laminated structure containing aligned collagen fibres and fibrocartilage and provides the major stabilizing structure to resist torsional and bending forces applied to the disc. The discs are contained between vertebral endplates comprised of hyaline cartilage that act as an intermediate layer between the hard vertebrae and the softer material of the disc.

The joints and musculoskeletal tissues of the human body are subject to traumatic injury and disease and degenerative processes that over a period of time can lead to the deterioration or failure of the joint causing severe pain or immobility. Generally, the ability of a load bearing joint to provide pain free articulation and carry load is dependent upon the presence of healthy bone, cartilage and associated musculoskeletal tissues that provide a stable joint. With reference to the spine, spinal disc degeneration, characterised by features such as loss of fluid, annular tears and myxomatous changes can result in discogenic pain and/or disc bulging or herniation of the nucleus in which the disc protrudes into an invertebral foramen comprising spinal nerves resulting in back pain and/or sciatica. This condition is more commonly referred to as a "slipped" disc.

To alleviate the condition described above, the damaged spinal disc may be surgically removed from the spine and the two adjacent vertebrae either side of the damaged disc fused together (arthrodesis). Although this technique successfully eliminates the symptoms of pain and discomfort and improves joint stability, it results in a total loss of movement of the fused vertebral joint and increases the stress placed on the adjacent joints leading to collateral damage of these joints and associated soft tissues. The degenerative cycle then begins anew.

A more desirable solution is to replace the damaged spinal disc with an artificial implant (arthroplasty) that allows full, pain free movement of the vertebrae and which mimics the function of a healthy spinal disc. Artificial spinal discs currently exist for use in such a procedure. However, the development of existing artificial discs has been limited, despite advances in biomaterials, because they lack the complexity of structure and cannot adequately mimic the biomechanics of a normal healthy human spinal disc.

Conventional artificial discs articulate using a bearing surface manufactured using metals, alloys or durable polymers including ultra-high molecular weight polyethylene. However, the use of hard, non-deformable bearing surfaces render the implant non-compliant and unable to replicate the compliant load bearing capacity provided by the natural disc. As a result, adjacent spinal levels are still exposed to increased mechanical stresses resulting in a high risk of further degeneration.

Compliant artificial spinal discs are generally either manufactured using a material of single uniform hardness (single durometer) or using two materials of differing hardness (dual durometer), in which case the material has a lower modulus core contained within a higher modulus shell. The former requires a compromise in material specification to balance strength and wear resistance with compliance whereas the latter often generates problems caused by a progressive failure along the interface between the two materials over a period of use. An artificial spinal disc of the latter type is known from U.S. Pat. No. 5,171,281.

A need therefore remains for an artificial spinal disc implant which can be surgically inserted in place of a damaged spinal disc and which will enable full, pain-free movement of the affected vertebral joint, which is durable enough to withstand the loads and wear imposed upon it in use without failing, and at the same time exhibit biomechanics which are as similar as possible to that of the body's own natural spinal discs and so can withstand both compression and torsional loading. If these requirements are not adequately met, and the artificial disc is too stiff, it will not deform sufficiently during movement and excessive deformation of the adjacent natural discs will occur. On the contrary, if the disc does not have the required degree of stiffness, excessive movement of the disc will occur causing it to bulge out resulting in pain and discomfort for the patient.

SUMMARY

According to an aspect of the invention, there is provided a process for making a polymeric product having a gradual variation in modulus through at least a portion of the product, comprising the steps of:

(a) reacting a multifunctional isocyanate, a polyol and, optionally, a chain extender, wherein at least two reagents selected from the isocyanate, the polyol, the chain extender, any mixture thereof and any pre-polymer formed therefrom, are intensively mixed to form a first polyurethane having a predetermined stoichiometry and thermal history;

(b) reacting a multifunctional isocyanate, a polyol and, optionally, a chain extender, wherein at least two reagents selected from the isocyanate, the polyol, the chain extender, any mixture thereof and any pre-polymer formed therefrom, are intensively mixed to form a second polyurethane having a predetermined stoichiometry and thermal history which is different to the stoichiometry and thermal history of the first polyurethane; and (c) injecting the first and second polyurethanes into a mould defining the polymeric product before the polymerisation reactions associated with the production of the first and second polyurethanes are complete so that polymerisation reactions between the first and second polyurethanes occur in the mould.

Although reference is made to first and second polyurethanes, it will be appreciated that the invention also includes within its scope a process involving more than two polyurethanes, each of which has a different predetermined stoichiometry and thermal history.

The modulus referred to is the modulus of elasticity or tensile modulus, also referred to as Young's Modulus, and is the ratio of stress to strain below the elastic limit. The Young's Modulus is calculated by dividing the strain into stress and provides a measure of the stiffness of the material.

The process preferably involves the step of injecting the first and second polyurethanes into the mould simultaneously. The polyurethanes may be injected at the same rate into the mould or, the relative rate of injection of the two polyurethanes into the mould may be altered so that more of one polyurethane is injected into the mould than the other thus providing a material that exhibits a graduation in modulus.

In one embodiment, the process includes the step of mixing the first and second polyurethanes prior to injection into the mould via a common injection port. Even when the polyurethanes are mixed prior to injection, it is possible to vary the relative rates of injection by varying the rate of delivery of each polyurethane.

Advantageously, the length of the common injection port may be altered to control the degree of interfacial mixing of the first and second polyurethanes prior to injection into the mould.

In one embodiment, the first and second polyurethanes may be formed simultaneously in separate apparatus. In this method, known as the dual head technique, two output streams, having different compositions, from two PPM machines (described in more detail below) are fed to a mould with two separate inputs at the same time. The input ports of the mould are so arranged to cause the mould to fill in a prearranged manner so that interfacial mixing of the two streams occurs resulting in the formation of a graded modulus structure. Alternatively, the two separate streams may be mixed prior to injection into the mould in which case they are injected through a common injection port.

A single PPM machine for producing the polyurethane may also be employed in which case the method includes the step of forming the first polyurethane, delivering it to an intermediate vessel and perturbing the relative amounts of the reagents being mixed by the machine to form the second polyurethane with a different stoichiometry.

The method may include the step of delivering the second polyurethane to an intermediate vessel.

The first and second polyurethanes are preferably injected into the mould from said intermediate vessels simultaneously.

The process preferably includes the step of controlling the temperature of each intermediate vessel to impart a known thermal history to the first and second polyurethanes contained therein.

According to another aspect of the invention, there is provided a process for making a polymeric product having a variable modulus through at least a portion of the product comprising the steps of:
(a) reacting a multifunctional isocyanate, a polyol and, optionally, a chain extender, wherein at least two reagents selected from the isocyanate, the polyol, the chain extender, any mixture thereof and any pre-polymer formed therefrom, are intensively mixed to form a polyurethane having a predetermined stoichiometry and thermal history;
(b) perturbing the relative amounts of said at least two reagents during the course of the reaction to continuously vary the modulus of the polyurethane so formed and,
(c) injecting the polyurethane into a mould defining the polymeric product before the polymerisation reactions associated with the production of the polyurethane is complete so that polymerisation continues in the mould.

The polyurethane may be passed through an extruder to be reactively extruded therein in the method according to either the first or second aspects of the invention.

The polyurethane may advantageously undergo thermal profiling during the reactive extrusion step.

According to another aspect of the invention, there is provided an apparatus for making a polymeric product having a gradual variation in modulus through at least a portion of the product comprising:
(a) a first delivery system for quantitatively dispensing at least two reagents selected from an isocyanate, a polyol, a chain extender, any mixture thereof and any pre-polymer formed therefrom; mixing means for intensively mixing said at least two reagents to form a first polyurethane having a predetermined stoichiometry.
(b) a second delivery system for quantitatively dispensing at least two reagents selected from an isocyanate, a polyol, a chain extender, any mixture thereof and any pre-polymer formed therefrom; mixing means for intensively mixing said at least two reagents and reactive extrusion means to form a second polyurethane having a different predetermined stoichiometry to that of the first polyurethane, and
(c) means for injecting the first and second polyurethanes into a mould before the polymerisation reactions associated with the formation of the first and second polyurethanes are complete so that polymerisation reactions between the first and second polyurethanes occur in the mould.

In one embodiment, the apparatus includes a common injection port for injecting the first and second polyurethanes into the mould simultaneously.

The apparatus may also include means for varying the relative amounts of the first and second polyurethanes injected into the mould or, the relative rates of injection of the first and second polyurethanes into the mould.

According to another aspect of the invention, there is provided an apparatus for making a polymeric product having a gradual variation in modulus through at least a portion of the product comprising:
(a) a delivery system for quantitatively dispensing at least two reagents selected from an isocyanate, a polyol, a chain extender, any mixture thereof and any pre-polymer formed therefrom; mixing means for intensively mixing said at least two reagents to form a first polyurethane having a predetermined stoichiometry.
(b) an intermediate vessel into which the first polyurethane is directed whilst the delivery system is used to quantitatively dispense at least two reagents selected from an isocyanate, a polyol, a chain extender, any mixture thereof and any pre-polymer formed therefrom; mixing means for intensively mixing said at least two reagents and reactive extrusion means to form a second polyurethane having a different predetermined stoichiometry to that of the first polyurethane, and
(c) means for injecting the first and second polyurethanes into a mould before the polymerisation reactions associated with the formation of the first and second polyurethanes are complete so that polymerisation reactions between the first and second polyurethanes occur in the mould.

In one embodiment, the apparatus includes a second intermediate vessel into which the second polyurethane is directed so that the first and second polyurethanes are injected from their respective vessels into the mould simultaneously. Alternatively, the first polyurethane is injected into the mould from an intermediate vessel and the second polyurethane is injected into the mould directly from the delivery system.

The apparatus may include a mix head to mix the first and second polyurethanes prior to injection into the mould. The mix head may also comprise means for altering the rate of injection into the mould, or rate of mixing, of each of the polyurethanes.

According to another aspect of the invention, there is provided an artificial spinal disc comprising a solid body of polymeric material that exhibits at least a portion having a gradual variation in modulus.

In a preferred embodiment, the modulus varies substantially linearly through said portion.

The artificial spinal disc preferably comprises a nucleus surrounded by an annulus region, said portion being located in a region between the nucleus and annulus regions.

The invention also provides an artificial spinal disc manufactured according to the process of the invention.

In one preferred embodiment for the manufacture of an artificial spinal disc, the two-part mould has a retractable central portion, the central portion being retracted after injection of polyurethane having a first stoichiometry and thermal history into the first part of the mould so as to form the annulus region so that the polyurethane having a second stoichiometry and thermal history can be injected into the second part of said mould so that polymerisation reactions between the polyurethanes injected into the first and second parts of the mould can occur in the mould to form a region between the two polyurethanes that exhibit a gradual variation in modulus.

The present invention also seeks to protect the use of the process according to the invention in the manufacture of an artificial spinal disc or any surgical device or implant.

A method of manufacturing polyurethane having a high degree of consistency making them suitable for use in the medical product industry is known as precision polyurethane manufacture (PPM) and is described in detail in the Applicant's own earlier International Application No. PCT/GB01/03441 (Publication No. WO 02/11975), to which reference is hereby made.

The PPM process enables the reagent stoichiometry and thermal profile to be controlled dynamically to reduce batch to batch property variation and WO 02/11975 specifically states that the reaction stoichiometry can be controlled within 0.01-2%, preferably within 0.05-1%, and most preferably within 0.1-0.2% and that the thermal profile of the resultant polyurethane can be controlled within 0.01-2° C., preferably within 0.05-1° C., and most preferably within 0.1-0.5° C., preferably using a computer. However, to date, no reference has been made to the application of the PPM process in the manufacture of a polymer product in which the reagent stoichiometry and thermal profile is purposively varied so as to produce a polymer product which exhibits a gradual variation in its modulus through the whole or part of that product.

In one embodiment, the polymer product comprises an artificial spinal disc. The graduation in the modulus of the material provides an artificial disc having all the benefits of a dual material design without any of the problems associated with the bonding of two dissimilar, separate components. The disc contains and constrains excessive deformation whilst maintaining the normal physiological motions of the spinal segment.

In a preferred embodiment, the artificial disc incorporates a set of polymeric end plates that exhibit a convex surface that engages with the surface of an adjacent vertebral body. In this preferred embodiment, the end-plates are manufactured as part of the complete device. Therefore, a portion of the device exhibits a gradual change in modulus as a function of distance from the surface of the body in an axial direction such that there are no interfacial bonds between the end-plates and the flexible core region of the spinal disc.

In an alternative embodiment, the end-plates are made from rigid materials such as biocompatible metal or polymer. In one embodiment, the variable modulus core may be firmly bonded to the end plates so that the end-plates are incorporated into the mould process and are not separate parts but actually covalently bonded with the core to provide a complete device. Conversely, the variable modulus core may be located, but not fixed, between the two end-plates to enable the core to slide between the end-plates.

BRIEF DESCRIPTION OF THE DRAWINGS

Embodiments of the present invention will now be described, by way of example only, with reference to the following drawings, in which.

DETAILED DESCRIPTION OF EMBODIMENTS

Figure 4:
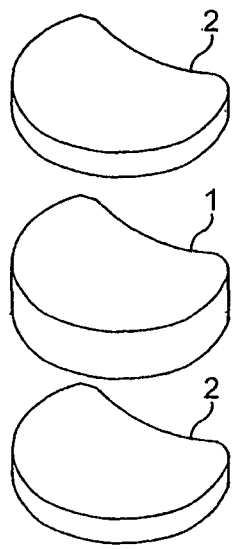
FIG. 4 shows a perspective view of an artificial spinal disc according to an embodiment of the invention together with endplates above and below the disc.

Referring firstly to FIG. 4, there is shown an artificial disc 1 together with a pair of end plates 2 used in conjunction with the disc 1. The disc 1 is a single unitary component having a soft elastomeric core region that mimics the function of the natural spinal disc nucleus and varies in volume by the total elastomer volume, and a peripheral region surrounding the core region exhibiting a graded modulus structure in which the modulus increases as a function of the distance from the nucleus region or decreases as a function of the distance from the surface of the disc 1. It will be appreciated that changing the relative volume of nucleus and annulus regions alter the overall mechanical performance of the complete device.

Therefore, the device structure can be modified to achieve optimum physiological performance.

In the preferred illustrated embodiment, the modulus varies from the surface of the disc to the nucleus. However, it will also be appreciated that the modulus may vary for only a portion of that distance. Although reference is made to a disc having a peripheral region and a core region, it will be appreciated that these regions are not separate or discrete and the disc is formed from one body of material.

Figure 5:
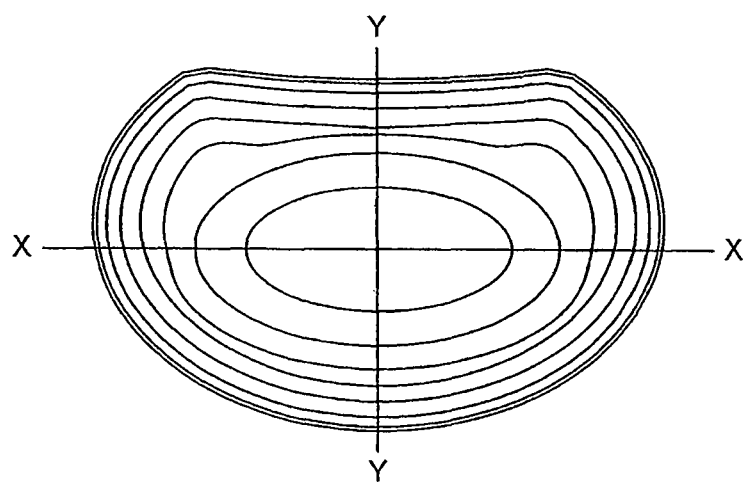
FIG. 5 shows a plan view of the disc shown in FIG. 4.
Figure 6:
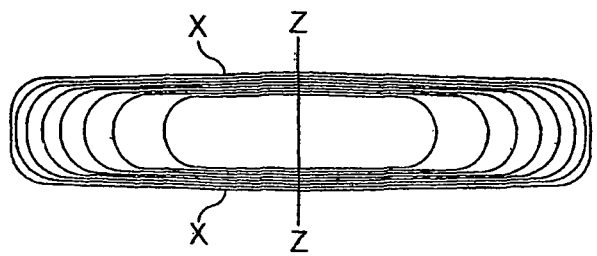
FIG. 6 shows a cross-sectional view along the line X-X in FIG. 5.
Figure 7:
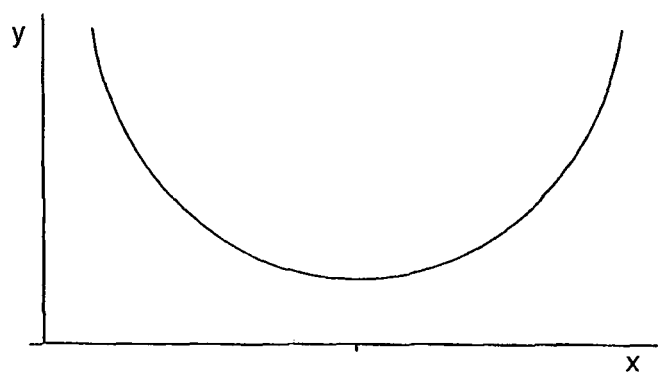
FIG. 7 is a graph showing the relationship between the modulus and distance through the disc in a radial direction indicated by X-X.
Figure 8:
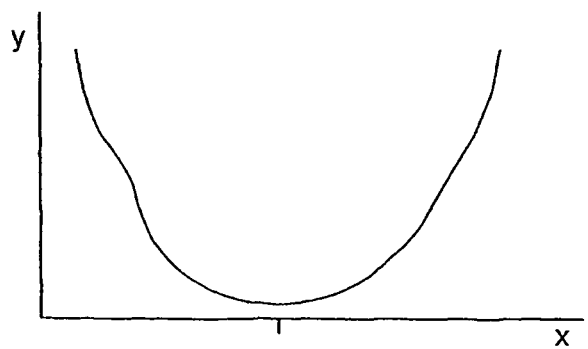
FIG. 8 is a graph showing the relationship between the modulus and the distance through the disc in a radial direction indicated by Y-Y in FIG. 5.
Figure 9:
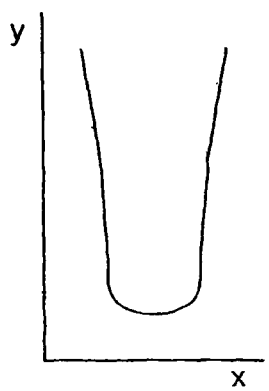
FIG. 9 is a graph showing the relationship between the modulus and the distance through the disc in an axial direction indicated by Z-Z in FIG. 6.

FIG. 5 shows a plan view of the spinal disc illustrated in FIG. 4 and FIG. 6 shows a cross-section through the disc along the line marked X-X in FIG. 5. Both views have been marked with contour lines showing the change in modulus through the disc, the modulus being greater where the lines lie close together. As can be seen from FIG. 5, the modulus increases as a function of the distance from the core region in a radial direction such as the directions indicated by X-X and Y-Y in FIG. 5, and this is shown in the plots of FIGS. 7 and 8. FIG. 7 illustrates a plot showing the relationship between the modulus (y-axis) against distance through the disc (x-axis). In FIG. 7, this distance is the radial distance along the line X-X in FIG. 5. In FIG. 8, the distance is the radial distance along the line Y-Y in FIG. 5. FIG. 9 also shows the change in modulus with respect to the distance through the article in an axial direction along the line Z-Z in FIG. 6. It can be seen from these graphs, that the material of the disc is anisotropic in that the modulus is different depending on the direction of measurement of the modulus through the disc.

In FIG. 4, the end plates 2 are shown separated from the disc for the purpose of the drawing only and are in intimate contact with upper and lower surfaces of the disc respectively when the disc is in use. The end plates 2 are usually bonded to the disc 1. However, they can also be unbonded but in close contact with the disc 1. The end plates 2 are constructed from any suitable metallic material or alloy that possesses sufficient stiffness to contain the disc and suitable fatigue strength for that purpose. In other embodiments, the end plates 2 may be provided with a structured surface with channels and bores suitable to promote bone ingrowth. The end plates 2 may also be coated with an osteoconductive ceramic such as hydroxy apatite. In a preferred embodiment the end-plates are formed as part of the complete device such that the end-plates are covalently bonded with the core. Thus, there is a change in modulus between the end-plates and core region See FIG. 6 in which the incorporated end-plates are labelled 'X'.

A disc 1 having the properties described above exhibits responses to compression and compression-torsion testing under simulated biomechanical loads that are similar to those exhibited by the natural spinal disc during movement of a human being and has mechanical properties (force penetration, recovery, creep) that ensures that the disc and the end plates deliver physiological appropriate motion (flexion, extension and torsion) to the adjacent vertebrae similar to those of a healthy spinal disc.

Although in a preferred embodiment the polymer product made using the method of the invention is an artificial spinal disc, it is envisaged that other devices or components for medical use could also be formed using one or other of the methods of the invention. One particular component is a variable modulus bearing surface that would replace at least a portion of damaged or degenerate articular cartilage within a synovial joint. This may include replacement of part of the adjacent bone to provide a reconstructed bearing surface. Examples include, but are not restricted to, an acetabular cup for use in hip arthroplasty procedures and a bearing surface to replace worn cartilage on the tibial plateau for arthroplasty procedures of the knee. These variable modulus bearing surfaces provide cushioning to the joint and increases congruency between articular surfaces during load bearing resulting in improved stress distribution and reduced contact stresses that will improve the fatigue life of the implant.

It is also envisaged that a variable modulus polymer could be used to replace or provide additional support to a complete bone or part of a bone in surgical procedures carried out for cosmetic as well as medical reasons.

An alternative embodiment for use in the medical industry is in the manufacture of an intravenous or urethral catheter which must have the required degree of stiffness to enable it to be passed through bodily conduits to reach the site of an occlusion but at the same time be flexible enough to prevent unnecessary trauma or collateral injury to the patient during an invasive procedure. It is envisaged that at least a portion of the elongate catheter may be formed from material having a gradual variation in modulus along its length.

The PPM process will now be described followed by an explanation of its application to the manufacture of a polymer product which exhibits a gradual variation in modulus.

The PPM process comprises reacting a multifunctional isocyanate, a polyol and, optionally, a chain extender, wherein at least two reagents selected from the isocyanate, the polyol, the chain extender, any mixture thereof and any pre-polymer formed therefrom, are intensively mixed prior to being reactively extruded, to form a polyurethane having a predetermined stoichiometry and thermal history. In the context of the present invention, the term "polyurethane" is understood to include any polymer which contains multiple urethane linkages and includes, for example, polyurethane-ureas. In an embodiment, at least a portion of the polyol or the chain extender is reacted with the isocyanate prior to extensive mixing, so as to "end-cap" the polyol or the chain extruder with isocyanate groups, thus facilitating subsequent reaction. In a modified arrangement, at least a portion of the isocyanate is reacted with the polyol or the chain extender prior to extensive mixing. Preferably, at least a portion of the chain extender is mixed with the polyol prior to intensive mixing. Advantageously, the process allows absolute control of reagent stoichiometry whilst intimate mixing of the reagents at the molecular level allows the manufacture of tailored linear polyurethanes of narrow molecular weight distribution or narrow polydispersity. Moreover, a known and reproducible thermal history can be imparted to the polymer during synthesis, whilst overall thermal degredation can be minimised by reducing the number of melt cycles for polyurethane components. Such a process allows the integrated manufacture of a polyurethane resin, finished product or aqueous polyurethane dispersion.

The multifunctional isocyanate may be any suitable aromatic, aliphatic or cycloaliphatic polyisocyanate, but is most preferably an organic diisocyanate. Preferred organic diisocyanates include 4,4'-diisocyanatodiphenylmethane, 2,4'-diisocyanatodiphenylmethane, isophorone diisocyanate, p-phenylene diisocyanate, 2,6-toluene diisocyanate, polyphenyl polymethylene polyisocyanate, 1,3-bis(isocyanatomethyl)cyclohexane, 1,4-diisocyanatocyclohexane, 1,6-hexamethylene diisocyanate, 1,5-naphthalene diisocyanate, 3,3'-dimethyl-4,4'-biphenyl diisocyanate, 4,4'-diisocyanatodicyclohexylmethane, 2,4'-diisocyanatodicyclohexylmethane, and 2,4-toluene diisocyanate, or combinations thereof. The polyol may be any suitable polyhydroxy compound, but is generally a hydroxy-terminated ester, ether or carbonate diol. Preferred polyalkylene ether glycols include polyethylene ether glycols, poly-1,2-propylene ether glycols, polytetramethylene ether glycols, poly-1,2-dimethylethylene ether glycols, poly-1,2-butylene ether glycol, and polydecamethylene ether glycols. Preferred polyester polyols include polybutylene adipate and polyethylene terephthalate. Preferred polycarbonate diols include polytetramethylene carbonate diol, polypentamethylene carbonate diol, polyhexamethylene carbonate diol, polyhexane-1,6-carbonate diol and poly[1,6-hexyl-1,2-ethyl carbonate]diol. However, many other suitable polyhydroxy compounds can also be used depending upon the desired application. The polymerisation reaction may be carried out in the presence of an activating amount of a suitable catalyst, for example, an organotin catalyst such as stannous octanoate. However, the presence of a catalyst is not usually necessary, due at least in part to the efficiency of the intensive mixing step, or even desirable, depending upon the intended application of the polyurethane, such as, for example, in implantable devices. For some applications, the multifunctional isocyanate and polyol are not reacted with a chain extender. In most cases, however, a chain extender will be included to effect chain extension or crosslinking of the urethane-linked pre-polymer as it forms. Any suitable polyol, polythiol or polyamine or mixture thereof that is suitable for this purpose may be used, such as, for example, mixed diols comprising a 2,4-dialkyl-1,5-pentanediol and a 2,2-dialkyl-1,3-propanediol. Specific examples of 2,4-dialkyl-1,5-pentanediol include 2,4-dimethyl-1,5-pentanediol, 2-ethyl-4-methyl-1,5-pentanediol, 2-methyl-4-propyl-1,5-pentanediol, 2,4-diethyl-1,5-pentanediol, 2-ethyl-4-propyl-1,5-pentanediol, 2,4-dipropyl-1,5-pentanediol, 2-isopropyl-4-methyl-1,5-pentanediol, 2-ethyl-4-isopropyl-1,5-pentanediol, 2,4-diisopropyl-1,5-pentanediol, 2-isopropyl-4-propyl-1,5-pentanediol, 2,4-dibutyl-1,5-pentanediol, 2,4-dipentyl-1,5-pentanediol, 2,4-dihexyl-1,5-pentanediol, and the like. Specific examples of 2,2-dialkyl-1,3-propanediol include 2,2-dipentyl-1,3-propanediol, 2,2-dihexyl-1,3-propanediol and the like. Especially preferred chain extenders include 1,4-butanediol, 1,2-ethylene diamine, hydrazine and triethylamine. However, many other suitable classes of polyols and amines are known to those skilled in the art are also included. In the context of the present invention, the phrase "intensively mixed" generally means that the two or more reagents selected from the isocyanate, the polyol, the chain extender, any mixture thereof and any pre-polymer formed therefrom, are intimately mixed at the molecular level. In a preferred embodiment, the two or more reagents are intensively mixed by vortexing, such that two or more reagent streams are caused to coincide and flow together in a spiral fashion. In another embodiment, the two or more reagents are transported via a swash plate pump or a gear pump. Most preferably, the two or more reagents are intensively mixed via a reactive injection processing technique, of the kind used in conventional RIM or SRIM processes. In a preferred embodiment, the synthesis technique of the current invention utilises an impingement mixing head, similar to those used in a RIM machine, and fitted with two or more reagent streams. Each different stream can be programmed to deliver the required amount of reagent continuously and with high accuracy not associated with current RIM or REX techniques. Moreover, as the reagents are intensively mixed at a molecular level, the reaction generally starts spontaneously, thereby avoiding the need for inclusion of reaction catalysts altogether or greatly reducing the amounts of such catalysts required. Since many of the catalysts normally used in such reactions are potentially highly toxic in vivo, the inventive process is particularly suitable for making polyurethane medical devices intended for implantation. The mix-head is preferably self-cleaning, to avoid having to clean the apparatus after each used. In an embodiment, the two or more reagents are delivered to the mix-head under pressure, preferably via one or more injection lances. For example, a first injection lance may contain isocyanate and a second injection lance may contain polyol and chain extender, or a first injection lance may contain a first isocyanate, a second injection lance may contain a second isocyanate mixed with an aliquot of a first polyol to effect end-capping, a third injection lance may contain a second polyol and a fourth injection lance may contain a chain extender. There are clearly many possible combinations and permutations of the various reagents and all of these combinations are intended to be included within the scope of the present invention. Preferably, the mixing step is substantially instantaneous, most preferably occurring within a time period of fraction of a second to a few seconds at most. It is especially desirable that the resultant mixture is substantially homogeneous immediately after mixing, although the subsequent composition of the mixture will obviously change as polymerisation proceeds. In the context of the present invention, the term "reactively extruded" is understood to mean that the physical and chemical properties of the polyurethane mixture are modified in a continuous flow stirred tank reactor (CSTR) or an extruder, preferably by at least one of the various forms of modification described above in relation to conventional REX procedures.

The resultant mixture may be fed directly into an extruder, the latter preferably being close coupled to the mix-head. The extruder may be immediately adjacent to and is, preferably, directly connected to the mix-head, such that the resultant polyurethane pre-polymer mixture exiting the mix-head passes straight into the extruder. The mixture may be fed into an extruder via a rheometer, a densitometer, a spectrophotometer or any combination thereof. This permits an instantaneous "snapshot" of the viscosity, density or composition of the reaction mixture to be taken before the reactive extrusion process begins and allows for any adjustments thereto to be made. Alternatively, the resultant mixture is fed into the extruder via a reaction chamber, preferably, a stirred reaction chamber, to allow further polymerization reactions to occur. Preferably, the mixture is fed into the extruder at a rate of 0.01-25 kg/s, preferably 0.1-10 kg/s, and most preferably 1-5 kg/s. The role of the extruder is essentially two fold. Firstly, the temperature of sections along the length of the extruder can be controlled, thereby controlling reaction temperature, which in turn dictates the progress of the polymerisation reaction. Secondly, as polymerisation reactions are taking place in the extruder, additional reagents can be introduced at the extruder and can participate in the polymerisation reaction to give modified polyurethanes of specific value, such as polyurethanes where the end group is different from the groups within the polymer chain. For example, a chain extender can be mixed with the pre-polymer at this stage, to promote chain extension or cross-linking and increase viscosity and molecular weight. Sensors can be placed along the length of the extruder barrel to monitor the reaction as it progresses, whilst temperature control means can be used to ensure that the reaction processes occur within defined temperature ranges. In a preferred embodiment, therefore, the polyurethane can be made to undergo thermal profiling during the reactive extrusion process, such that it has a well-defined thermal history. The extruder may also comprise a rheometer, a densitometer, a spectrophotometer or any combination thereof at a pre-determined point along its length or at its exit, such that the physical and chemical properties of the forming polymer and the final polyurethane can be closely monitored and, if necessary, adjusted during the reactive extrusion process.

It is also known to provide an apparatus for making a polyurethane using the PPM process comprising: a delivery system for quantitatively dispensing at least two reagents selected from an isocyanate, a polyol, a chain extender, any mixture thereof and any pre-polymer formed therefrom; mixing means for intensively mixing said at least two reagents; and reactive extrusion means. The delivery system comprises one or more injection lances, preferably controlled by the use of linear transducers. The reactive extrusion means comprises a barrel extruder, preferably having one or more entry ports for introduction of various reagents. Preferably, the reactive extrusion means is a twin screw extruder, most preferably a co-rotating twin screw extruder. Any commercially available twin screw extruder may be used, such as an APV Baker MP2030 with a 30 mm screw diameter (L: D=40/1; D=30 mm) co-rotating twin screws and sixteen heating zones, which is available from APV Baker, Speedwell Road, Parkhouse East, Newcastle-under-Lyme, United Kingdom. The extruder can be provided with at least one thermocouple, to monitor the temperature of extruded material in the immediate vicinity of the thermocouple. The extruder may also be provided with temperature regulating means, to control the temperature of the extruded material in the region adjacent thereto and the apparatus may include measurement means adapted to measure a physical or chemical parameter or property of the polyurethane mixture. Preferably, the measurement means comprise a rheometer, a densitometer, a spectrophotometer or any combination thereof located between the mixing means and the reactive extrusion means, so as to enable an instantaneous assessment of the properties of the polyurethane or pre-polymer mixture to be made, prior to reactive extrusion. The apparatus also comprises at least one measurement means within or at the exit of the reactive extrusion means to monitor the properties of the polyurethane mixture and the final polymer. The apparatus may further comprise: means for controlling the rate at which the delivery means dispenses said at least two reagents in response to a first control signal; means for controlling the rate at which the resultant mixture is fed to the reactive extrusion means in response to a second control signal; means for controlling the temperature of the polyurethane mixture in the reactive extrusion means in response to a third control signal; means for detecting a property of the polyurethane mixture during reactive extrusion and being adapted to generate a detector signal; and a processor adapted to generate said first, second and third control signals in response to said detector signal. This enables the inventive process to be automated and any necessary adjustments required to produce a polyurethane of well defined or pre-determined stoichiometry and thermal history to be accurately controlled. In this last mentioned embodiment, the control and detection means are preferably programmable means, such that their operation can be controlled by a program run on a computer.

Figure 1:
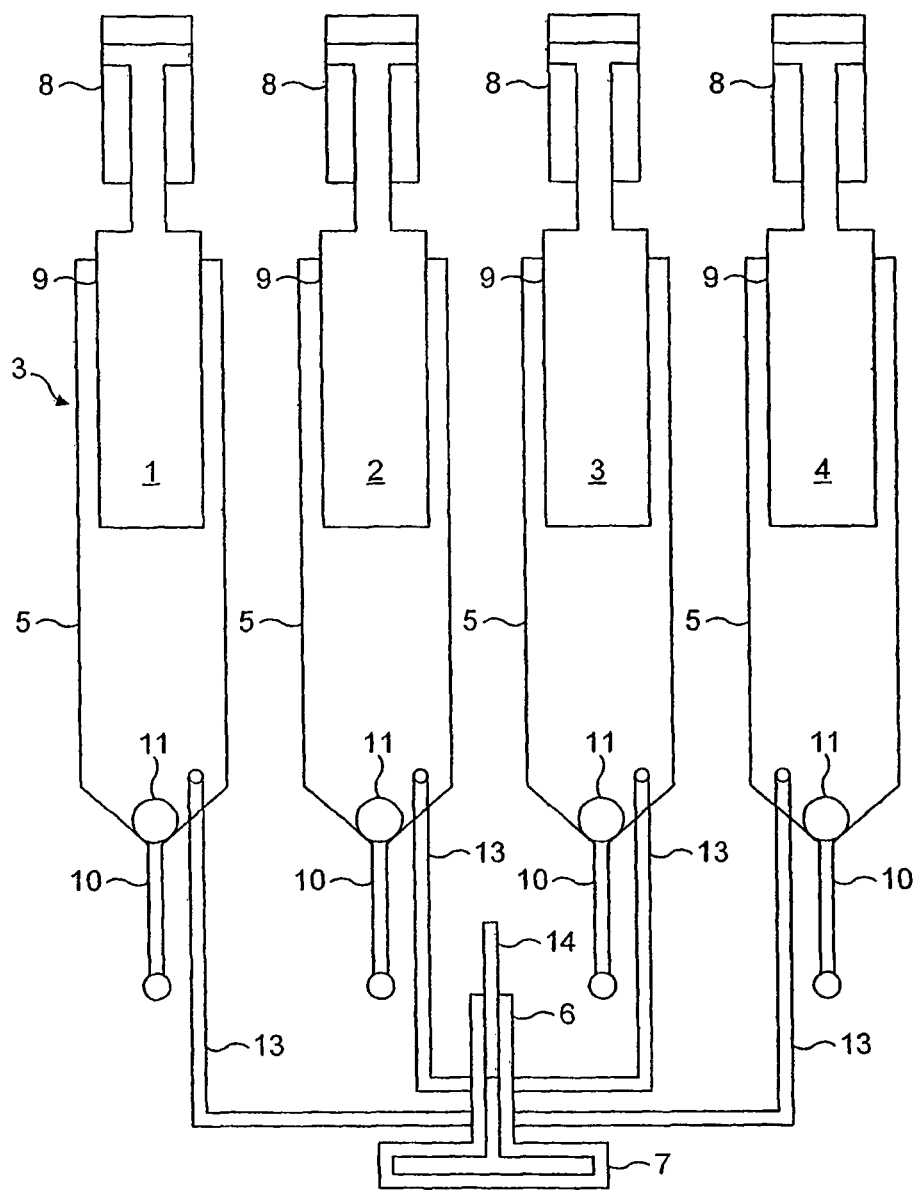
FIG. 1 illustrates a front view of the reactive injection moulding apparatus that comprises four injection lances.

The PPM apparatus 3 is illustrated in FIG. 1 and comprises four injection lances 5, a four reagent stream mix head 6 and a mould 7. It will be appreciated that the process is not limited to the use of 4 lances and that there may be 5 or 6 or more depending on the number of materials to be manufactured. This means that more than just two polyurethanes with different stoichiometries can be made and mixed together to get a more complex variable modulus product. It will be appreciated that may involve more than just two intermediate vessels.

Each lance 5 is numbered for ease of identification and comprises a hydraulic cylinder 8, a lance pump 9, an inlet pipe 10, a non-return valve 11 and an outlet pipe 13. The mix head 6 is adapted so that both pairs of reagent streams from the four outlet pipes 13 directly oppose each other. The mix head 6 comprises a cylindrical mix-pin 14 having four vertical grooves (not shown) that are inscribed into the surface of the cylinder at equal intervals and run along ⅜ths of its length from the mid point to within ⅛$^{th}$ of its length from the bottom face of the pin 14.

Figure 2:
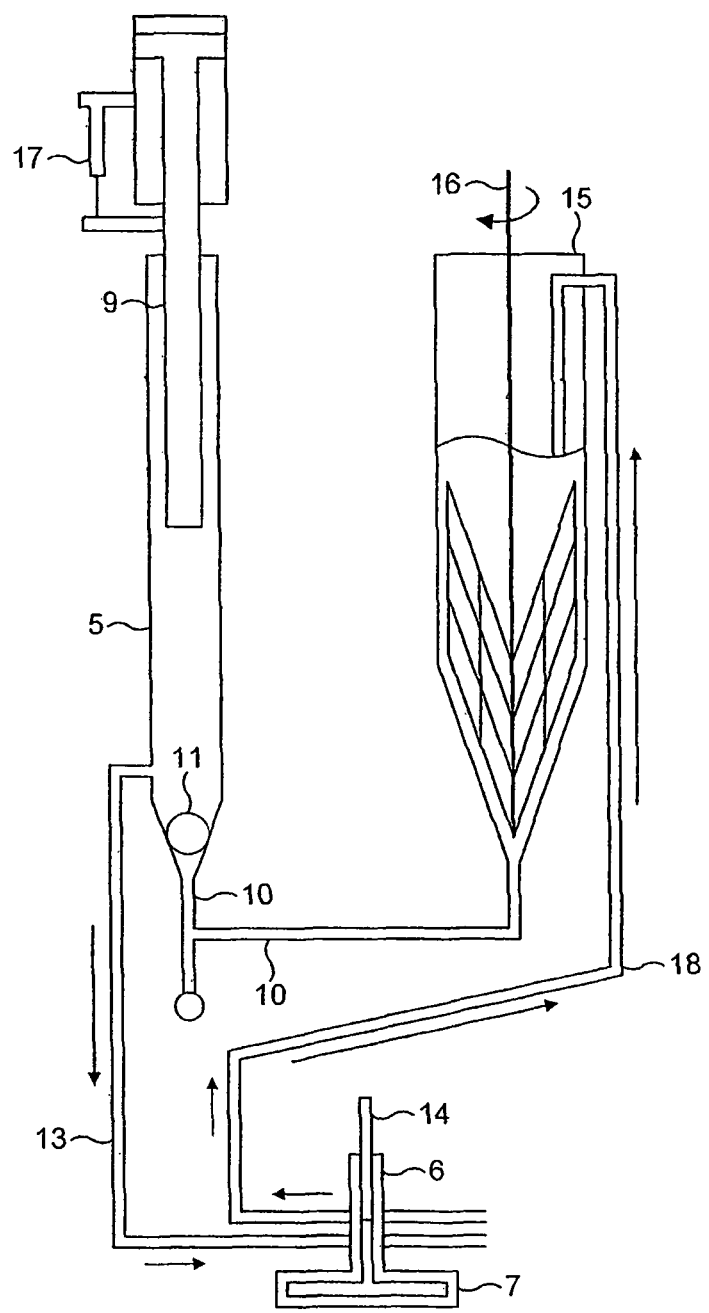
FIG. 2 illustrates a side view of one of the injection lances of the reaction injection moulding apparatus of FIG. 1.

Referring to FIG. 2, each lance 5 is supplied with reagent from mix tank 15 which is stirred by a paddle stirrer 16. Reagent is supplied to lance 5 via inlet pipe 10, passing through non-return valve 11. Reagent is drawn from mix-tank 15 into lance 5 by raising lance pump 9 and subsequently ejected from lance 5 by depression of lance pump 9 through the action of hydraulic cylinder 8 controlled by means of a linear transducer 17 controlled by means of a personal computer (not shown). Reagent is supplied to mix-head 6 via outlet pipes 13. When mix pin 10 is fully inserted into mix head 6, the grooves align with the outlet pipes 9 to provide channels to the return pipes 18, such that the reagent streams are recycled to mix-tanks 15 without being able to enter the mould 7. When mix-pin 10 is retracted so that its lower face sits between outlet pipes 13 and the return pipes 18, the reagents are impingement mixed before passing into mould 7. When mould 7 is full, mix pin 10 is again fully inserted allowing excess reagents to be recycled to mix tanks 15 via return pipes 18.

Figure 3:
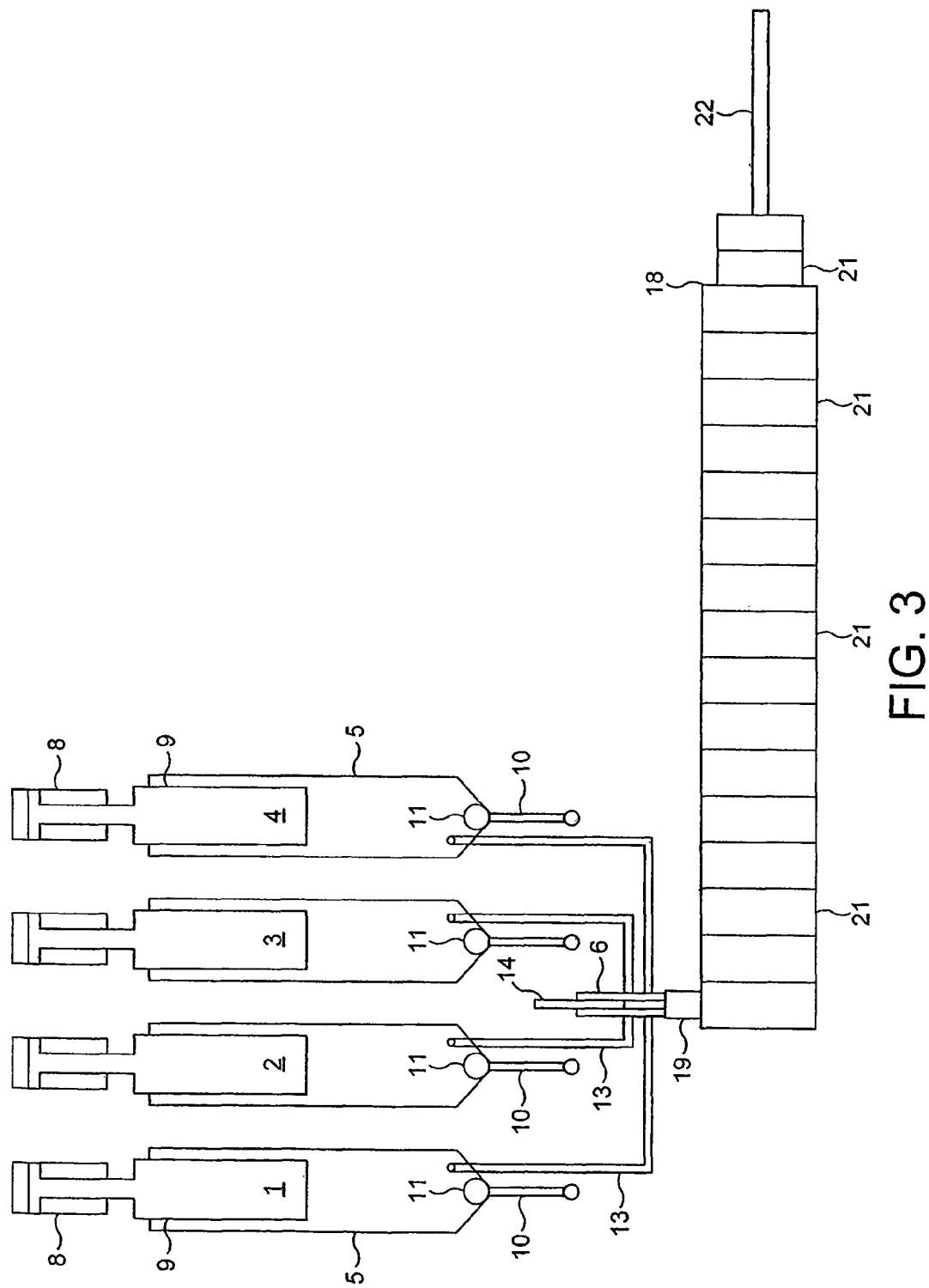
FIG. 3 illustrates a front view of a PPM apparatus that include lances and extruder.

FIG. 3 illustrates the complete PPM manufacturing apparatus that comprises four injection lances 5, a mix head 6 and an extruder 18. The extruder 18 is joined to the mix head 6 via a rheometer 19 and has 30 mm diameter co-rotating twin screws (not shown), sixteen programmable heating zones 20, a second rheometer 21 and a die 22. It will be appreciated that alternative forms of extruders can also be used depending on the application. When mix pin is retracted, mixed reagents from mix head pass via rheometer 19 into the extruder 18. Reaction mixture passes through each of the heating zones 20 which are programmed to maintain the mixture at a predetermined temperature before exiting the extruder 18.

In a typical run, the mix-tanks are pre-heated to the required temperature and then charged with the required amount of reagents, as determined by the stoichiometry, sequence distribution requirements and length of production run required. The reagents are continuously stirred by paddle stirrers under nitrogen until homogenous and at constant temperature. A "dry" run is carried out (where the mix-head pin is not retracted) under the required reaction conditions, that is, stream mix-ratios, mix-volume and mix-time. The pressure of each stream is monitored during this run. The pressure in each stream can be balanced if necessary by adjustment of a needle valve behind the mix-head orifice (not shown). Balancing the pressure of each stream is essential, as it facilitates good mixing as well as preventing the reaction from taking place in the supply lines, which will occur if the pressure of one stream is significantly greater than the other streams, thereby filling the stream feed line. The reagents in each tank are circulated using the lances, with the lances drawing the reagents from the holding tank and ejecting them around the circuit and back into the holding tank. When ready to run, the control software is launched. The size (volume) of each lance is programmed into the software, and can be changed if required. Several pieces of information are requested by the software, namely: streams to be used, mix-volume, mix-time, and mix-ratio. The "streams to be used" information activates the required lances. The mix-volume is the total amount of product required at the end of the run, with the maximum volume being the sum of the selected stream volumes. The mix-time determines the time that the mix-pin is retracted and the velocity of the lances. The mix ratio determines the ratio of the velocities of the lances. From this information, the software calculates the ideal dispensing requirements. For example, using the following parameters for 2 lances of equal size, 1 L mix-volume, 4 seconds mix-time and a mix-ratio of 1:1, 0.5 L from each stream is mixed over a period of 4 seconds. If a mix-ratio of 3:1 were required, 0.75 L of the first stream would be impingement mixed with 0.25 L of the second stream (with the velocity of the first stream being three times that of the second stream). The software becomes invaluable when using more streams of different sizes and different mix-ratios. The position of each lance is measured with the linear transducer. After the above information is entered into the software, the contents of the lances are ejected and the "empty" reading from the transducers taken. The lances are then filled completely, and the "full" reading taken.

When the apparatus is ready to run, the lances 5 eject reagents into the respective transfer lines. The velocity of each lance 5 is monitored by software and, when constant, the mix pin 14 is retracted allowing impingement mixing of the reagents in the mix head 6. The mixed reagents undergo rapid polymerisation reactions as they pass from the mix head 6 into the close coupled twin screw extruder via an in-line rheometer 19. The reacting mixture passes through the extruder 18 in a predetermined time and follows a predetermined thermal profile dictated by the combination of the running speed of the extruder 18 and the temperature settings of each of the programmed temperature zones 20. An in-line rheometer 21 is fitted at the output end of the extruder 18 to give real time measurement of rheological properties which are used as a signal to control aspects of the operation of the process, such as extruder speed, temperature of the extruder zones, lance speed, stoichiometry, reagent temperature, in accordance with an algorithm operated by a computer, to give real time control of the rheological properties of the polyurethane.

A product having a gradual variation in modulus is produced according to one embodiment of the invention by forming two polyurethanes each having a different stoichiometry and/or thermal history and formed either one after the other using the same PPM machine or, simultaneously using two separate PPM machines. If the polyurethanes so produced are intensively mixed prior to injection into a mould, or are injected separately into the mould so that they mix within it prior to completion of the polymerisation reactions taking place, the reactions will continue between the two polyurethanes once in the mould resulting in a product exhibiting a variation in modulus through it. The polyurethanes formed using the same or different machines may be stored in an intermediate vessel prior to injection into the mould. If the same machine is being used to produce both polyurethanes, the first polyurethane may be stored in an intermediate vessel whilst the second polyurethane is formed by perturbing the relative amounts of the reagents to change the stoichiometry of the polyurethane emerging from the machine. The second polyurethane may be injected directly into the mould together with the first polyurethane from the intermediate vessel. Alternatively, the second polyurethane may be stored in another intermediate vessel so that both polyurethanes may be injected into the mould from their respective vessels. The temperature of each vessel may be independently controlled to impart a different thermal history and/or viscosity to each of the polyurethanes stored in the intermediate vessels. As already mentioned above, each of the polyurethanes can be fed through an extruder having independently controllable temperature sections do that the reaction temperature and hence the progress of the polymerisation can be controlled.

The polyurethane can also be made to undergo thermal profiling during the reactive extrusion process such that it has a well defined thermal history.

Of particular interest to the Applicants lies in the evaluation of the flow of reacting polyurethane systems into a three-dimensional (3-D) mould cavity that is suitable for the manufacture of spinal disc prostheses. Consequently, the aim is to provide accurate 3-D placement of material within the moulding cavity with the ideal result being a peripheral (annulus) material surrounding a central core (nucleus) region with the nucleus material being symmetrical from the mid-point on the vertical plane but with a significant lateral distribution, as has already been described with reference to FIGS. 2 to 6. Several parameters which affect this distribution are outlined below:

1. Material properties—viscosity, contact angle of the material.
2. Injection Speed—With reference to a spinal disc, the injection speed of annulus and nucleus materials are different to achieve the correct distribution.
3. Injection port geometry—this will influence the flow of material into the mould. With reference to a spinal disc, injection port geometry will influence the distribution of the nucleus material.

Many of these parameters can be varied to achieve optimum conditions for the control of the 3-D distribution of materials within a mould. For example, material viscosity can be influenced by the temperature of the mould and/or intermediate vessel, injection rate is determined by the dispense rate from the intermediate vessel and an optimum injection port geometry can be machined to provide the desired conditions. In contrast, the contact angle is dependent upon the properties of the injected material and the material used to manufactured the mould e.g. aluminium, steel etc. Furthermore, a commercially available release agent e.g. silicone, will also influence the interaction between injected material and mould walls. Understanding the influence of the contact angle will enable the injection rate and injection port geometry to be modified accordingly to achieve the desired 3-D distribution of material properties.

Several examples of how these parameters influence the 3-D distribution of material properties within a mould for the manufacture of variable modulus device such as an artificial spinal disc prostheses will now be given.

Figure 10A:
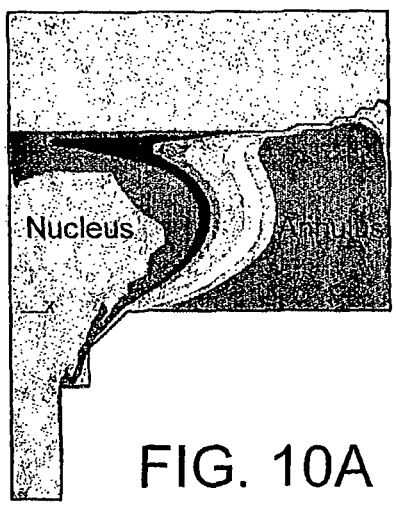
FIGS. 10A, 10B & 10C show the distribution of material properties in a mould during the manufacture of an artificial spinal disc according to some specific examples.

An axisymmetric finite element (FE) model of a flat mould (10 mm height, 20 mm radius) was constructed and validated experimentally using moulds with the same geometry and volume. The following parameters were used (values given are approximate):
Viscosity Material A=5000 cP
Viscosity Material B=15000 cP
Contact angle of material with mould surface=60 degrees.
Injection Speeds=0.100 ml/s and 0.010 ml/s For the purpose of this first example, Material 'A' will from the annulus and Material 'B' will form the nucleus and the injection rate will be altered to illustrate the change in 3-D distribution of material within the mould. The resulting distribution of material properties using a constant injection rate of 0.010 ml/s and 0.100 ml/s are illustrated in FIG. 10A/Table 1 and FIG. 10B/Table 2 respectively. The annulus and nucleus regions are indicated in the diagrams together with an intermediate region that exhibits a variation in modulus between the nucleus and annulus properties. For the purpose of this example the variation in modulus is generated by interfacial mixing within the injection port prior to the bulk flow reaching the mould (not shown in this example).

TABLE 1

| Nucleus Viscosity (cP) | Annulus Viscosity (cP) | Injection Speed (ml/s) | Contact Angle (Degree) |
|---|---|---|---|
| 15000 | 5000 | 0.010 | 60 |

TABLE 2

| Nucleus Viscosity (cP) | Annulus Viscosity (cP) | Injection Speed (ml/s) | Contact Angle (Degree) |
|---|---|---|---|
| 15000 | 5000 | 0.100 | 60 |

Figure 10B:
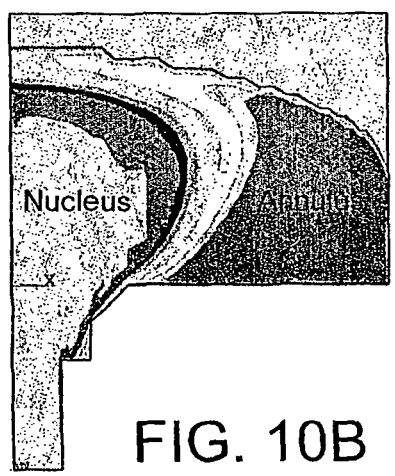

It is clear from the illustrations that a low nucleus injection speed provides a nucleus region that is located lower in the mould (FIG. 10A) whereas higher injection speeds provide a nucleus region located at the top of the mould (FIG. 10B). It will be appreciated that an optimum speed for a given mould geometry and material properties will provide a product that exhibits symmetry in the vertical plane. Furthermore, injection rate will also determine the distribution of material properties in a radial direction. For the example provided, slower injection speeds provide a nucleus material that exhibits a greater radial distribution compared to higher injection speeds. With reference to a spinal disc, optimisation of the injection speed for annulus and nucleus materials would provide a nucleus material that is located at the centre of the mould encapsulated by annulus material. In the same way, the distribution of material that exhibits a gradual variation in modulus between annulus and nucleus regions can also be precisely controlled.

It will be appreciated that the extent of material distribution within the product will also be influenced by mould geometry, injection port geometry and material properties and the injection rate should be modified accordingly to achieve the desired material distribution.

Figure 10C:
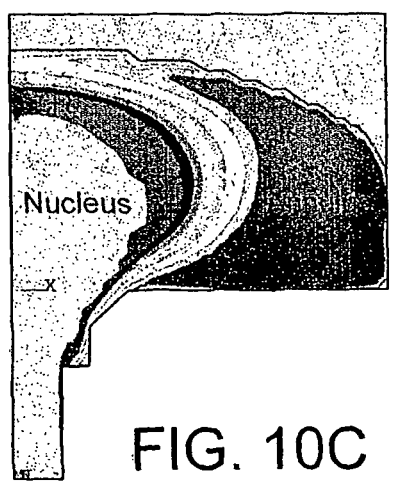

A further example using the same model demonstrates the influence of nucleus and annulus material properties. FIG. 10C and Table 3 illustrates the distribution of material properties in a mould that consists of a nucleus (Material 'A') and annulus (Material 'B') and results from using an injection speed that is equivalent to that used in FIG. 10B. It will be appreciated that despite the vertical momentum provided by the bulk flow of material through the injection port, the lower viscosity nucleus is unable to penetrate through the high viscosity annulus material at the surface. Consequently, the nucleus material is distributed in a radial direction to provide a nucleus region that exhibits greater vertical and radial symmetry in comparison to the material distribution illustrated in FIG. 10B.

TABLE 3

| Nucleus Viscosity (cP) | Annulus Viscosity (cP) | Injection Speed (ml/s) | Contact Angle (Degree) |
|---|---|---|---|
| 5000 | 15000 | 0.100 | 60 |

It will be appreciated from the foregoing examples that the manufacture of a variable modulus product requires precise control of the speed of material delivery; particularly when fabricating devices or components with a relatively small volume such as a spinal disc prosthesis.

Whilst the example provided describes the distribution of properties within a mould suitable for the manufacture of variable modulus prostheses, the same principles and inventive technology are applicable to other mould geometries and variable modulus products that require accurate 3-D placement of the material.

The following section provides some more detail of how a variation in modulus can be achieved as a result of varying the relative contributions of different materials from two intermediate vessels.

Figure 11:
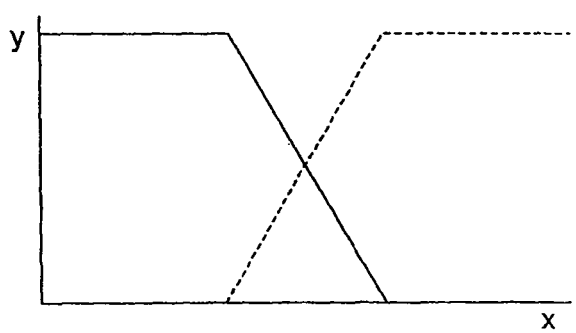
FIG. 11 is a graph to show how a material that has a gradual modulus can be formed by varying the amounts of two materials injected into a mould.
Figure 12:
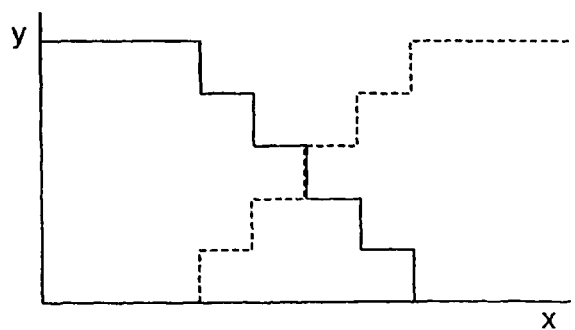
FIG. 12 is a graph to show how a material that has a gradual modulus can be formed by having a step or incremental change in the relative amounts of materials injected into the mould.

Manufacture of a device that exhibits a gradual variation in modulus from one material (A) to another (B) can be achieved by varying the relative amounts of materials dispensed from the intermediate vessels. An example of this process is represented by the graph of FIG. 11 in which the Y-axis is the percentage of material and the X-axis is the time. At the start of the injection process only material A (solid line) is injected into the mould. After a given time, injection of material A is retarded whilst the injection of material B (dashed line) begins such that the relative amounts of both materials is continuously varied. Alternatively, the variation in modulus between two or more materials may be generated by having a step or incremental change in the relative amounts of materials injected into the mould as represented in the graph of FIG. 12.

It will be appreciated that the extent of the region of graduated modulus will be governed by the rate at which the injection of materials A and B are varied.

With reference to the manufacture of a spinal disc, material A is injected first to form the annulus. Injection of material A is then retarded as the flow of material B is increased to generate a variation in material properties prior to injection of 100% of material B to form the nucleus region of the spinal disc. Manufacturing parameters described above are optimised for the spinal disc mould geometry and material properties and a suitable injection speed for annulus and nucleus materials chosen accordingly to provide the desired 3-D distribution of material properties within the mould.

In the method, known as step perturbation, the relative amounts of the at least two reagents are perturbed during the course of the reaction so as to continuously vary the modulus of the polyurethane so formed. The polyurethane is then injected into a mould defining the polymeric product.

In another proposed method, the output from the reaction injection moulding machine may be continuous and of a fixed composition. However, the PPM process may include an extruder through which the polymer is passed. The extruder may be provided with multiple ports along its length and mould may be filled with material sampled from each port. The material from each port may be processed differently to provide materials that possess a different modulus. A layer of material from each port is then fed into the mould and the layers diffuse into each other to provide a final component having a variable modulus. The component may also undergo a post compression stage at high temperature to form the final product and increase the degree of diffusion of the layers into each other to provide a product having a more gradual change in modulus.

In accordance with the methods of the invention, a region that exhibits a variation in modulus between the two materials can arise through several processes. First, as mentioned previously, materials are injected one after the other and a variation in modulus arises through interfacial mixing between the materials. Second, materials are injected through a common injection port that allows interfacial mixing within the injection tube prior to flow reaching the mould. In this regard, the extent of the graded modulus may be modified according to the length of the injection nozzle which determines the extent of mixing between materials prior to the flow entering the mould. An alternative method involves passing continuously varied amounts of each material through a static mixer or length of tube, to achieve a resultant material that exhibits a continual change in properties. This method relies upon precise control of the material dispense cylinders to achieve a variation in the relative amount of material dispensed from each delivery stream.

Alternatively, the intermediate vessel may be a mould or carousel. The intermediate vessel is maintained at adequate temperature and the material reacts to form a slug. At the required moment this slug can be injected into a cavity mould having the shape of the required component. As the material is held in the carousel, it enables the reactant to consolidate and a known thermal history to be imparted into the product.

These materials may be produced using one PPM machine that switches between the manufacture of different materials to maintain the level of material contained within the dispense cylinders. However, these methods are not confined to use with a single PPM or Reaction Injection Moulding machines. Alternatively, if larger flow rates are required, two PPM machines maybe employed to manufacture each material separately to ensure a continual flow of materials into the dispense cylinders. It will be appreciated that other material manufacturing methods or arrangements of the PPM apparatus could be used to feed the dispense cylinders to enable manufacture of devices and components that exhibit a variation in modulus.

The intermediate vessel may alternatively be an injection moulding machine barrel or syringe. The material may then be injected directly into the required mould.

Many modifications and variations of the invention will be apparent to those skilled in the art and the foregoing description should be regarded as a description of the preferred embodiments only.

The invention claimed is:

1. An artificial spinal disc implant comprising a body of polymeric material, wherein the body has a solid unitary polymeric portion exhibiting a gradual variation in Young's modulus, wherein the body includes a nucleus region and an annulus region surrounding the nucleus region, and the gradual variation in Young's modulus is in a direction from the nucleus region to the annulus region and the artificial spinal disc implant is constructed and arranged for placement between adjacent vertebrae.

2. An artificial spinal disc implant according to claim 1, wherein the artificial spinal disc implant is designed to include a load bearing surface.

3. An artificial spinal disc implant according to claim 1, wherein the body has an upper surface, a lower surface and a sidewall between the upper surface and the lower surface, wherein the annulus region separates the nucleus region from the upper surface, the lower surface, and the sidewall.

4. An artificial spinal disc implant according to claim 1, wherein a Young's modulus of the nucleus region is less than a Young's modulus of the annulus region.

5. An artificial spinal disc implant according to claim 1, wherein the unitary portion is between the nucleus region and the annulus region and the Young's modulus increases across the unitary portion with increasing distance from the nucleus region.

6. An artificial spinal disc implant according to claim 1, wherein the unitary portion is located within the annulus region and the Young's modulus increases across the unitary portion with increasing distance from the nucleus region.

7. An artificial spinal disc implant according to claim 1, wherein the Young's modulus is increased with increasing distance from the nucleus region in a radial direction.

8. An artificial spinal disc implant according to claim 1, wherein the Young's modulus is increased with increasing distance from the nucleus region in an axial direction.

9. An artificial spinal disc implant according to claim 1, wherein the variation in Young's modulus in the body is anisotropic.

10. An artificial spinal disc implant according to claim 1, wherein the body comprises a polyurethane material.

11. An artificial spinal disc implant according to claim 10, wherein the body comprises a first polyurethane material having a first stoichiometry and a second polyurethane material having a second stoichiometry.

12. An artificial spinal disc implant according to claim 11, wherein the body comprises a nucleus region and an annulus region, the nucleus region comprising the first polyurethane material and the annulus region comprising the second polyurethane material.

13. An artificial spinal disc implant according to claim 1, wherein the unitary portion exhibiting a gradual variation in Young's modulus is pre-determined.

14. An artificial spinal disc implant according to claim 1, wherein the Young's modulus varies substantially linearly through the unitary portion.

15. An artificial spinal disc implant according to claim 1, including a pair of integral polymeric end plates configured such that there are no interfacial bonds between the end plates and a remainder of the artificial spinal disc implant.

16. An artificial spinal disc implant according to claim 1, further comprising a first end plate on an upper surface of the body and a second end plate on a lower surface of the body.

17. An artificial spinal disc implant according to claim 16, wherein at least one of the end plates has a convex outer surface.

18. An artificial spinal disc implant according to claim 16, wherein outer surfaces of at least one of the end plates define channels.

19. An artificial spinal disc implant according to claim 16, wherein the first and second end plates are integral with the body.

20. An artificial spinal disc implant according to claim 16, wherein there are no distinct interfaces between the first and second end plates and the body.

21. An artificial spinal disc implant according to claim 16, wherein the first and second end plates are covalently bonded to the body.

22. An artificial spinal disc implant according to claim 16, wherein the first and second end plates and the body form a unitary structure.

23. An artificial spinal disc implant according to claim 16, wherein at least one of the end plates is coated.

24. An artificial spinal disc implant according to claim 16, wherein the first and second end plates comprise polymeric material.

25. An artificial spinal disc implant according to claim 16, wherein the artificial spinal disc implant is entirely formed of polymeric material.

26. An artificial spinal disc implant according to claim 1, wherein the variation in Young's modulus is continuous across the portion.

* * * * *